United States Patent

Illian et al.

[11] Patent Number: 5,366,657
[45] Date of Patent: Nov. 22, 1994

[54] GEMINAL DIMETHYLALKYL COMPOUNDS, PROCESS FOR THEIR PREPARATION AND THEIR USE IN LIQUID-CRYSTALLINE MIXTURES

[75] Inventors: Gerhard Illian, Frankfurt am Main; Ingrid Müller, Hofheim, both of Germany; Takamasa Harada, Chiba, Japan

[73] Assignee: Hoechst Aktiengesellschaft, Frankfurt am Main, Germany

[21] Appl. No.: 915,687

[22] PCT Filed: Jan. 24, 1991

[86] PCT No.: PCT/EP91/00129
§ 371 Date: Jul. 24, 1992
§ 102(e) Date: Jul. 24, 1992

[87] PCT Pub. No.: WO91/11441
PCT Pub. Date: Aug. 8, 1991

[30] Foreign Application Priority Data
Feb. 2, 1990 [DE] Germany .................. 4003012

[51] Int. Cl.$^5$ .............. C09K 19/06; C09K 19/34; C09K 19/12; C09K 19/20
[52] U.S. Cl. .............. 252/299.6; 252/299.61; 252/299.66; 252/299.67; 544/298; 548/136
[58] Field of Search .......... 252/299.01, 299.6, 299.61, 252/299.66, 299.67; 544/298; 548/136

[56] References Cited

U.S. PATENT DOCUMENTS

| | | | |
|---|---|---|---|
| 4,504,403 | 3/1985 | Tsunemi et al. | 252/68 |
| 4,880,561 | 11/1989 | Tabohashi et al. | 252/299.61 |
| 4,886,614 | 12/1989 | Yoshimura et al. | 252/79 |
| 4,975,112 | 12/1990 | Griffin et al. | 71/92 |
| 4,980,352 | 12/1990 | Schwartz et al. | 514/253 |
| 5,085,792 | 2/1992 | Narihiko et al. | 252/79 |

FOREIGN PATENT DOCUMENTS 0315455 5/1989 European Pat. Off. .
0335348 10/1989 European Pat. Off. .

*Primary Examiner*—Robert L. Stoll
*Assistant Examiner*—C. Harris
*Attorney, Agent, or Firm*—Curtis, Morris & Safford

[57] ABSTRACT

Geminal dimethylalkyl compounds, process for their preparation and their use in liquid-crystalline mixtures Geminal dimethylalkyl compounds of the formula (I)

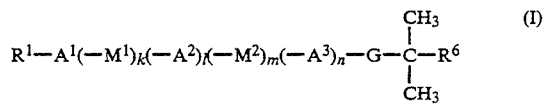

in which:
$R^1$ is, for example, straight-chain or branched (with or without an asymmetric carbon atom) alkyl or alkenyl having 2 to 16 carbon atoms,
$A^1$, $A^2$ and $A^3$ are, for example, identical or different 1,4-phenylene, 1,4-cyclohexylene or pyrimidine-2,5-diyl,
$M^1$ and $M^2$ are, for example, identical or different CO—O or O—CO,
G is for example, identical or different straight-chain or branched alkylene having 1 to 16 carbon atoms,
k, l, m and n are zero or 1, and
$R^6$ is straight-cain alkyl having 1 to 10 carbon atoms,
can advantageously be employed in liquid-crystalline mixtures. In liquid-crystalline mixtures, said compounds result in a melting point depression, in a shift in the temperature limit of the $S_c$ phase in ferroelectric mixtures and in other improvements of important electro-optical characteristic values.

11 Claims, No Drawings

GEMINAL DIMETHYLALKYL COMPOUNDS, PROCESS FOR THEIR PREPARATION AND THEIR USE IN LIQUID-CRYSTALLINE MIXTURES

DESCRIPTION

The unusual combination of anisotropic and fluid behavior of liquid crystals has resulted in their use in a wide range of electrooptical switching and display devices. In these, their electrical, magnetic, elastic and/or thermal properties can be utilized to give changes in alignment. Optical effects can be achieved, for example, with the aid of birefringence, the inclusion of dye molecules which absorb dichroically ("guest-host mode") or light scattering.

In order to satisfy the ever increasing demands of practice in the various fields of application, there is a constant demand for novel improved liquid-crystal mixtures and thus also for a large number of mesogenic compounds of various structures. This applies both in the areas where nematic LC phases (for example TN="twisted nematic" STN="supertwisted nematic", SBE="super-twisted birefringence effect", ECB="electrically controlled birefringence") are used and also in those having smectic LC phases (for example ferroelectric or electroclinic).

Many of the compounds which are suitable for LC mixtures may be described by a structure principle [see, for example, J. Am. Chem. Soc., Vol. 108, 4736 (1986), Structure I; Science, Vol. 231, 350 (1986), FIG. 1 A; J. Am. Chem. Soc., Vol. 108, 5210 (1986), FIG. 3] in which rings from cyclic compounds—aromatics, heteroaromatics or alternatively saturated ring systems—are linked to alkyl side chains which are straight-chain or substituted in the chain by small groups (for example methyl or chlorine) and are thus mono-branched.

Recently, there has been increasing interest in ferroelectric liquid-crystal systems as display elements in electrooptical components. A prerequisite for such systems to be usable in practice is frequently the formation of a smectic C phase or a chiral smectic C phase ($S_c$ or $S_c^*$ phase) in a broad temperature range, in particular also at temperatures around and below room temperature. In most known compounds which form an $S_c$ phase, this is formed at a temperature considerably above room temperature. The object is therefore to reduce the melting point and in particular the lower phase-transition point of the $S_c$ phase.

It is known that the melting point depression in mixtures is the more pronounced the greater the structural difference between the components of the mixture (see, for example, J. Chem. Soc. 1955, 4305). This also applies to the melting point depression in systems which have a phase sequence $C \rightleftarrows S_c \rightleftarrows S_A \rightleftarrows N \rightleftarrows I$ which is ideal for the production of electrooptical components. However, other essential characteristic values tend to be retained here if the components of the mixture are structurally similar. The two objects—melting point depression and shift of the lower temperature limit of the $S_c$ phase to lower temperatures on the one hand and as far as possible production of the other characteristic values on the other hand—are thus contradictory.

It has now been found that geminal dimethylalkyl compounds of the formula (I) satisfy said demands,

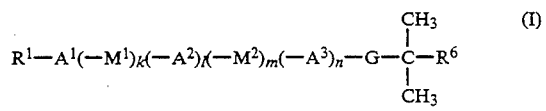

in which:

$R^1$ is $CH_3$, straight-chain or branched (with or without an asymmetric carbon atom) alkyl or alkenyl having 2 to 16 carbon atoms, it also being possible for one or two non-adjacent —$CH_2$— groups to be replaced by —O—, —S—, —CO—, —CO—O—, —O—CO—, —Si(CH$_3$)$_2$— or —O—O—, and it also being possible for H of the alkyl radical to be replaced by F, or is one of the following radicals

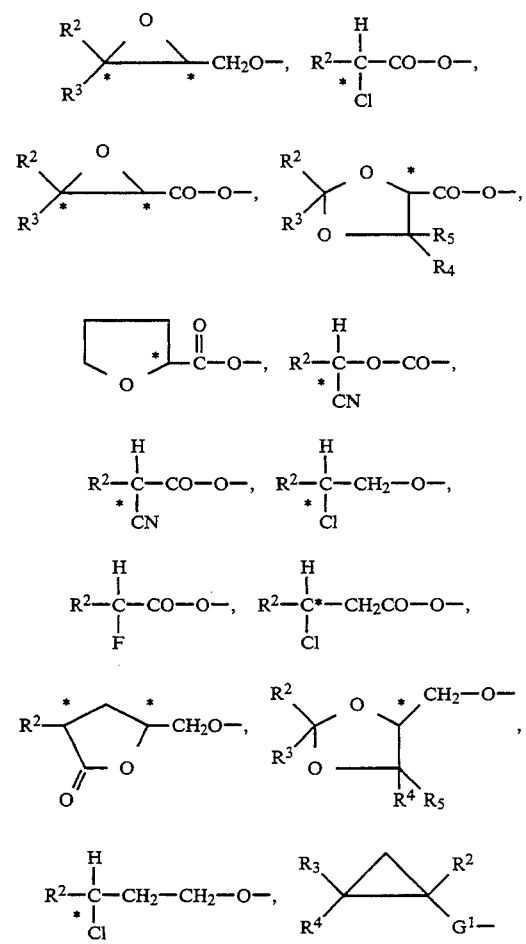

$A^1$, $A^2$ and $A^3$ are identical or different 1,4-phenylene, in which 2H may be replaced by F, 1,4-cyclohexylene, pyrazine-2,5-diyl, pyridazine-3,6-diyl, pyridine-2,5-diyl, pyrimidine-2,5-diyl or (1,3,4)-thiadiazole-2,5-diyl, $M^1$ and $M^2$ are identical or different —CO—O—, —O—CO—, —CO—S—, —S—CO—, —CH$_2$—O—, —O—CH$_2$—, —C≡C— or G and $G^1$ are identical or different straight-chain or branched alkylene having 1 to 16 carbon atoms in which, in addition, one or two non-adjacent —CH$_2$— groups may be replaced by —O—, —S—, —O—CO—, —CO— O—, —CO— or —O—CO—O—, $R^2$, $R^3$, $R^4$ and $R^5$ are identical or different, H or straight-chain or branched alkyl having 1 to 16 carbon atoms or alkenyl having 2 to 16 carbon atoms in which, in addition, one —CH$_2$— group may be replaced by —O—, —S—, —CO—O—, —O—CO—, —CO—, or —O—CO—O—, k, l, m and n are zero or 1, and $R^6$ is straight-chain alkyl having 1 to 10 carbon atoms.

Preference is given here to geminal dimethylalkyl compounds in which, in the formula I, the —A$^1$(—M$^1$)$_k$(—A$^2$)$_l$(—M$^2$)$_m$(—A$^3$)$_n$— group is:

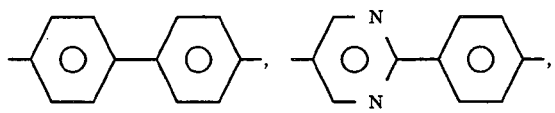

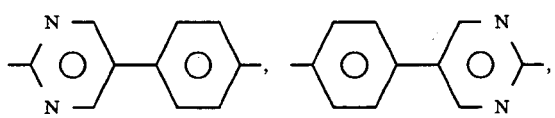

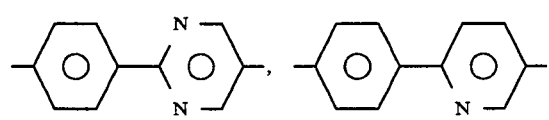

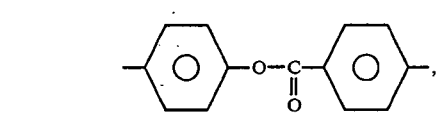

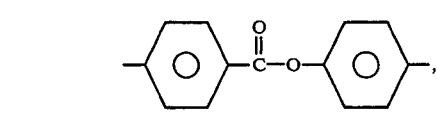

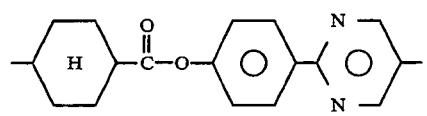

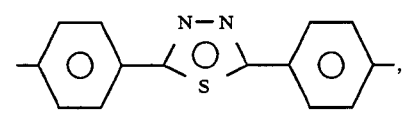

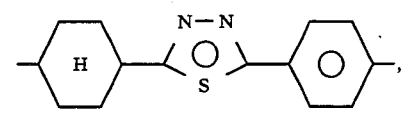

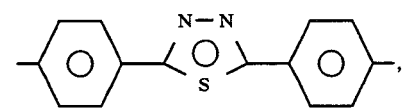

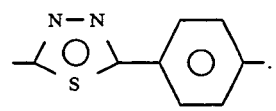

Particular preference is given to geminal dimethylalkyl compounds in which, in the formula I, the —A$^1$-(—M$^1$)$_k$(—A$^2$)$_l$(—M$^2$)$_m$(—A$^3$)$_n$— group has the following meanings:

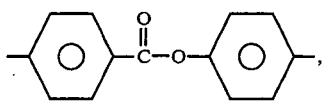

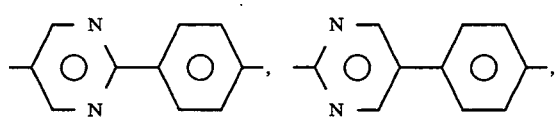

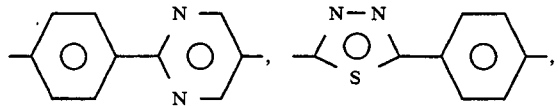

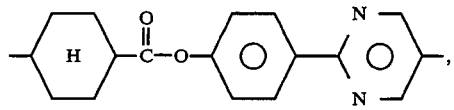

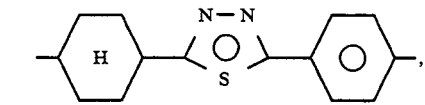

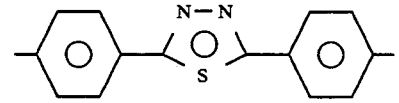

$R^1$ is: straight-chain or branched (with or without an asymmetric carbon atom) alkyl or alkenyl having 2 to 16 carbon atoms, it also being possible for one CH$_2$ group to be replaced by —O—, —S—, —CO—, —CO—O— or —O—CO—, G is: straight-chain or branched alkylene having 1 to 16 carbon atoms in which, in addition, one —CH$_2$— group may be replaced by —O—, —S—, —CO—O— or —O—CO—, and $R^6$ is: straight-chain alkyl having 1 to 6 carbon atoms.

The novel geminal dimethyl-substituted compounds are chemically, photochemically and thermally stable and have good mixture compatibility. Of the compounds of the formula (I), particular preference is given to phenylbenzoates and to those in which at least one of the radicals A$^1$, A$^2$ and A$^3$ is 1,4-phenylene and another is pyrimidine-2,5-diyl or 1,3,4-thiadiazole-2,5-diyl.

The abovementioned compounds are distinguished by the fact that, compared with the analogous alkyl compounds which are not geminally disubstituted, they have in some cases significantly lower melting points. The melting point is crucially dependent on the position of the dimethyl group in the chain.

It has become apparent that particularly low melting points and broad liquid-crystalline phase ranges are obtained if the alkylene or alkyl chains G and R$^6$ (see formula I) contain, independently of one another, between 2 and 8, particularly preferably 4 or 5, —CH$_2$— units. For low melting points, a total number of —CH$_2$— units in G and R$^6$ in the dimethyl-substituted chain of between 7 and 12 is advantageous, and particularly favorable properties are obtained in chains having 8 or 9 —CH$_2$— chain members.

An outstanding feature of the geminally branched dimethyl compounds is their good properties in mixtures. Thus, they have not only good mixture compatibility, but also affect, in a particular manner, the melting point of mixtures. It could be observed that the use of the dimethyl-substituted compounds of the formula (I) according to the invention in liquid-crystalline mixtures results in significant melting point depressions and/or in a likewise advantageous shift in the crystallization temperature toward very low temperatures.

These properties make the compounds particularly interesting as constituents of liquid-crystalline mixtures. Particular preference is given to the use of dimethyl-substituted compounds of the phenylpyrimidines, phenylbenzoates and phenylthiadiazoles in mixtures.

Specifically for ferroelectric mixtures, the use of the dimethyl-substituted components according to the invention brings, in addition to the favorable properties with respect to the depression both of the crystallization point and of the melting point, further particular advantages. Thus, it could be observed that the use of the compounds of the formula (I) results in a significant shortening of the switching times. A further advantage is that the dimethyl-substituted dopes induce significantly higher spontaneous polarizations compared with the unsubstituted dopes.

In addition, it could be shown that the compounds according to the invention have a higher effective switching angle than the corresponding alkyl compounds and thus induce better transmission in the bright state in the electrooptical switching element.

Preferred components for increasing the effective switching angle are the phenylbenzoates and the 5-phenylpyrimidin-2-yl compounds.

A further solution of the object set is a liquid-crystalline mixture which contains at least one compound of the formula (I).

The liquid-crystal mixtures comprise 2 to 20, preferably 2 to 15, components, including at least one of the compounds claimed according to the invention. The other constituents are preferably selected from the known compounds having nematic, cholesteric and/or tilted smectic phases, including, for example, Schiff's bases, biphenyls, terphenyls, phenylcyclohexanes, cyclohexylbiphenyls, pyrimidines, cinnamic acid esters, cholesterol esters, and various bridged polynuclear esters of p-alkylbenzoic acids with terminal polar groups.

In general, the commercially available liquid-crystal mixtures exist, even before addition of the compound(s) according to the invention, as mixtures of various components, of which at least one is mesogenic, i.e. as a compound which, in a derivatized form or mixed with certain components, exhibits a liquid-crystal phase [gives rise to expectations of at least one enantiotropic (clear point > melting point) or monotropic (clear point < melting point) mesophase formation].

The liquid-crystal mixtures generally contain from 0.01 to 70% by weight, preferably from 0.05 to 50% by weight, in particular from 0.1 to 25% by weight, of the compound(s) according to the invention.

The compounds according to the invention may be prepared by standard reactions known per se from mesogenic mono-functional-reactive parent structures by linking to likewise monofunctional-reactive geminal dimethylalkyl compounds, the synthesis of the two components being as known.

Liquid-crystalline mixtures which contain compounds of the formula (I) are particularly suitable for use in electrooptical switching and display devices (displays). Switching and display devices (LC displays) contain, inter alia, the following constituents: a liquid-crystalline medium, outer plates (for example made of glass or plastic), coated with transparent electrodes, at least one alignment layer, spacers, sealing frames, polarizers and, for color displays, thin colored filter layers. Further possible components are anti-reflection, passivation, compensation and barrier layers and electrically nonlinear elements, such as, for example, thin-film transistors (TFT) and metal-insulator-metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12-30 and 163-172).

The invention is illustrated by the examples below.

EXAMPLES

To prepare the illustrative compounds:

The compounds according to the invention can be prepared by standard reactions known from the literature from mesogenic monofunctional parent structures by linking to likewise monofunctional geminal dimethyl compounds.

The synthesis of the mesogenic starting materials is known from the literature. The geminal dimethyl compounds can be prepared, for example, by the method of J. Org. Chem., Volume 35, 3218 (1970).

EXAMPLE 1

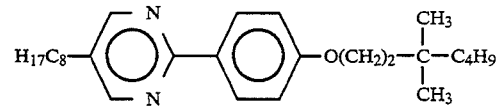

Preparation 0.8 ml (5 mmol) of diethyl azodicarboxylate are added dropwise at a temperature of from 0° to 5° C. to 1.3 g (5 mmol) of triphenylphosphine in 30 ml of methylene chloride. The mixture is stirred at room temperature for 30 minutes, and 1.42 g (5 mmol) of 4-(5-octylpyrimidin-2-yl)phenol and 0.72 g (5 mmol) of 3,3-dimethylheptanol are then added. After a reaction time of 48 hours, the solvent is removed by distillation and the residue is purified by chromatography (silica gel/methylene chloride/ethyl acetate (98:2)).

Recrystallization from methanol gives 0.5 g of colorless crystals.

The phase sequence is: X 34 I.

EXAMPLE 2

The following is obtained analogously:

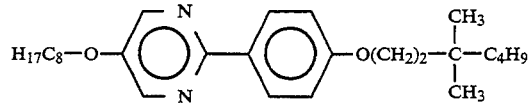

5-Octyloxy-2-[4-(3,3-dimethylheptyl)oxyphenyl]-pyridine

Phase sequence: X 57 $S_c$ 51 $S_A$ 53 I.

EXAMPLE 3

H$_{17}$C$_8$—[pyrimidine]—[phenyl]—O(CH$_2$)$_2$—C(CH$_3$)(CH$_3$)—C$_6$H$_{13}$ Phase sequence: X 36 I.

EXAMPLE 4

H$_{17}$C$_8$O—[pyrimidine]—[phenyl]—O(CH$_2$)$_2$—C(CH$_3$)(CH$_3$)—C$_6$H$_{13}$ Phase sequence: X 46 S$_A$ 44 I.

EXAMPLE 5

H$_{17}$C$_8$—[pyrimidine]—[phenyl]—O(CH$_2$)$_4$—C(CH$_3$)(CH$_3$)—C$_4$H$_9$

Phase sequence: X −1 S$_c$ 19 S$_A$ 29 I.

The effect of the position of the dimethyl branch can be seen by comparing the phases of the compounds from Examples 1, 3, 5 and 7. It is clear that the compound from Example 5 has particularly favorable properties. The melting point of this compound is 20° to 35° C. lower than in the compounds from the other examples. The dimethyl substitution in the 5-position obviously results in a particularly low melting point compared with the 3-position or 7-position.

Comparative Example C5

A comparison with the compound from Example 5 is offered by the following compound, which differs from the compound from Example 5 essentially by the fact that it contains no dimethyl branch.

H$_{17}$C$_8$—[pyrimidine]—[phenyl]—O—C$_9$H$_{19}$

Phase sequence (see Flüssige Kristalle in Tabelle I [Liquid Crystals in Table I], Deutscher Verlag für Grundstoffindustrie VEB (Leipzig), 1974, page 260, No. 4169):

X 33 S$_c$ 56 S$_A$ 65 N 68 I.

The compound according to the invention has a melting point which is 34° C. lower than C5.

EXAMPLE 6

H$_{17}$C$_8$O—[pyrimidine]—[phenyl]—O(CH$_2$)$_4$—C(CH$_3$)(CH$_3$)—C$_4$H$_9$

Phase sequence: X$_1$ 35 X$_2$ 17 S$_c$ 64 S$_A$ 67 I.

Comparative Example C6

A comparison with the compound from Example 6 is offered by the following compound:

C$_8$H$_{17}$—O—[pyrimidine]—[phenyl]—O—C$_8$H$_{17}$

This has the following phase sequence: X 51 S$_c$ 92.3 S$_A$ 99.5 N 100.3 I.

The substance according to the invention has a melting point which is 15° C. lower.

EXAMPLE 7

H$_{17}$C$_8$—[pyrimidine]—[phenyl]—O(CH$_2$)$_6$—C(CH$_3$)(CH$_3$)—C$_2$H$_5$

Phase sequence: X 18 S$_c$ 36 S$_A$ 51 I.

EXAMPLE 8

H$_{17}$C$_8$—O—[pyrimidine]—[phenyl]—O(CH$_2$)$_6$—C(CH$_3$)(CH$_3$)—C$_4$H$_9$ Phase sequence: X$_1$ 22 X$_2$ 36 S$_c$ 74 S$_A$ 82 I.

Comparative Example C8

A comparison with Example 8 is offered by the following non-dimethyl-substituted compound:

H$_{17}$C$_8$—O—[pyrimidine]—[phenyl]—O—C$_{10}$H$_{21}$

Phase sequence: X 50 S$_c$ 89 S$_A$ 99.6 I.

The compound according to the invention has the advantage that its melting point is 14° C. lower.

EXAMPLE 9

H$_9$C$_4$—C(CH$_3$)(CH$_3$)—(CH$_2$)$_2$—O—[pyrimidine]—[phenyl]—OC$_8$H$_{17}$ Phase sequence: X 48 I.

EXAMPLE 10

H$_{13}$C$_6$—C(CH$_3$)(CH$_3$)—(CH$_2$)$_2$—O—[pyrimidine]—[phenyl]—OC$_8$H$_{17}$ Phase sequence: X 59 I.

EXAMPLE 11

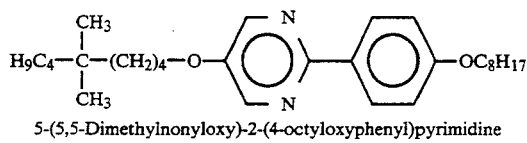

5-(5,5-Dimethylnonyloxy)-2-(4-octyloxyphenyl)pyrimidine

Phase sequence: X 54 $S_c$ 34 N 37 I.

EXAMPLE 12

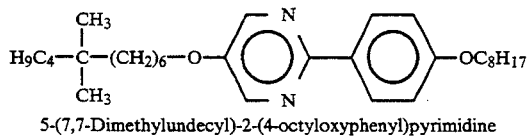

5-(7,7-Dimethylundecyl)-2-(4-octyloxyphenyl)pyrimidine

Phase sequence: X 43 $S_c$ 55 I.

Compared with illustrative compound 11, this substance has a melting point which is 11° C. lower.

A chain length of 11 carbons is obviously preferable to a chain length of 9 carbons.

EXAMPLE 13

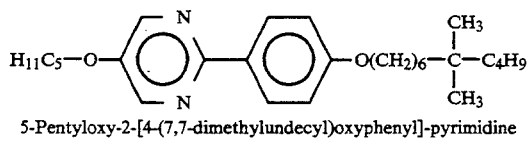

5-Pentyloxy-2-[4-(7,7-dimethylundecyl)oxyphenyl]-pyrimidine

Phase sequence: X 62 $S_c$ 35 $S_A$ 63 I.

EXAMPLE 14

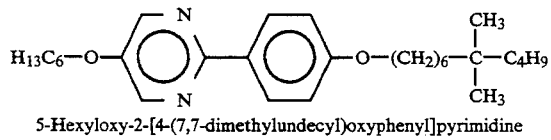

5-Hexyloxy-2-[4-(7,7-dimethylundecyl)oxyphenyl]pyrimidine

Phase sequence: X 31 $S_c$ 34 $S_A$ 77 I.

EXAMPLE 15

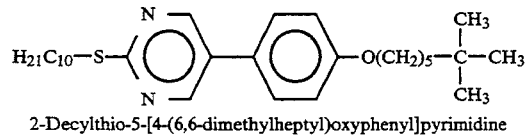

2-Decylthio-5-[4-(6,6-dimethylheptyl)oxyphenyl]pyrimidine

Phase sequence: X 60 $S_c$ 53 $S_A$ 55 I.

EXAMPLE 16

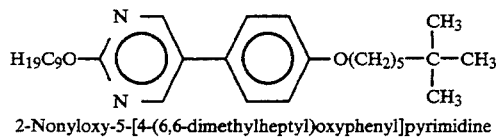

2-Nonyloxy-5-[4-(6,6-dimethylheptyl)oxyphenyl]pyrimidine

Phase sequence: X 86 $S_c$ 80 $S_A$ 82 I.

EXAMPLE 17

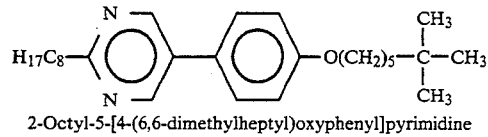

2-Octyl-5-[4-(6,6-dimethylheptyl)oxyphenyl]pyrimidine

Phase sequence: X 73 $S_c$ 64 $S_A$ 71 I.

EXAMPLE 18

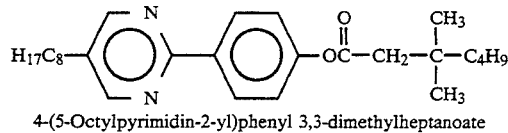

4-(5-Octylpyrimidin-2-yl)phenyl 3,3-dimethylheptanoate

Phase sequence: X 34 I.

EXAMPLE 19

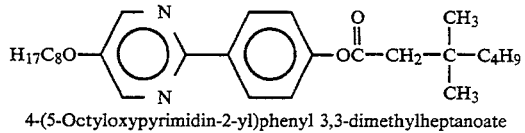

4-(5-Octyloxypyrimidin-2-yl)phenyl 3,3-dimethylheptanoate

Phase sequence: X 53 $S_c$ 49 N 50 I.

Comparative Example 19

A comparative component which differs essentially from Example 19 in that it contains no geminal dimethoxy group has the phase sequence:
X 73 $S_c$ 89 $S_A$ 92 N 93.

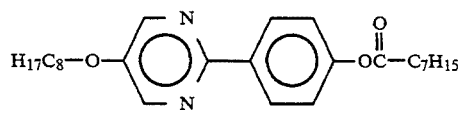

By contrast, the substance according to the invention has a melting point which is 20° C. lower.

EXAMPLE 20

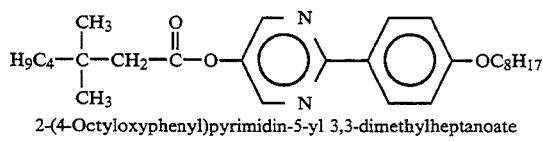

2-(4-Octyloxyphenyl)pyrimidin-5-yl 3,3-dimethylheptanoate

Phase sequence: $X_1$ 48 $X_2$ 54 I.

EXAMPLE 21

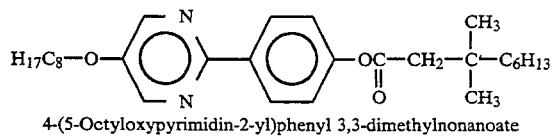

4-(5-Octyloxypyrimidin-2-yl)phenyl 3,3-dimethylnonanoate

Phase sequence: X 45 $S_c$ 42 N 46 I.

EXAMPLE 22

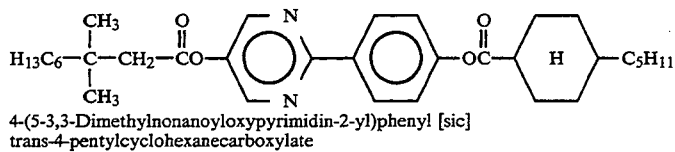

4-(5-3,3-Dimethylnonanoyloxypyrimidin-2-yl)phenyl [sic] trans-4-pentylcyclohexanecarboxylate Phase sequence: X 102 N 119 I.

EXAMPLE 23

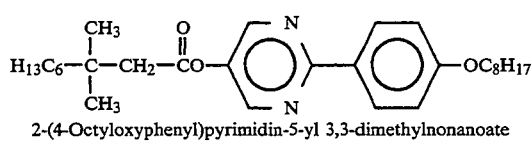

2-(4-Octyloxyphenyl)pyrimidin-5-yl 3,3-dimethylnonanoate

Phase sequence: X 61 I.

EXAMPLE 24

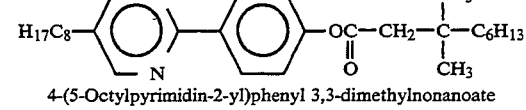

4-(5-Octylpyrimidin-2-yl)phenyl 3,3-dimethylnonanoate

Phase sequence: X 45 I.

EXAMPLE 25

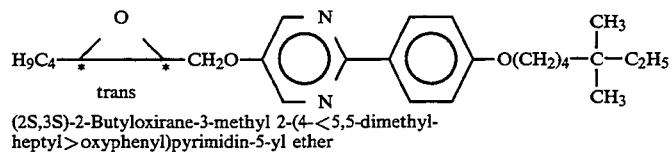

5-(1,1-Dimethylnonyl)-2-(4-octyloxyphenyl)pyrimidine

Phase sequence: X 22 I.

EXAMPLE 26

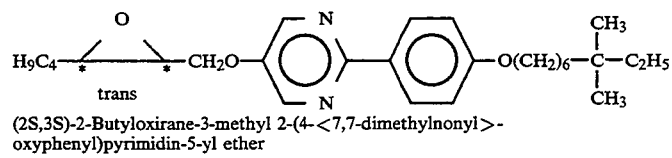

(2S,3S)-2-Butyloxirane-3-methyl 2-(4-<5,5-dimethylheptyl>oxyphenyl)pyrimidin-5-yl ether Phase sequence: X 83 $S_2$ 87 $S_A$ 92 I. $[\alpha]_D^{22} = -18.06°$ (c=2, $CH_2Cl_2$)

EXAMPLE 27

(2S,3S)-2-Butyloxirane-3-methyl 2-(4-<7,7-dimethylnonyl>-oxyphenyl)pyrimidin-5-yl ether Phase sequence: X 90 $S_c$ 96 $S_A$ 106 I. $[\alpha]_D^{22} = -17.16°$ (c=2, $CH_2Cl_2$)

EXAMPLE 28

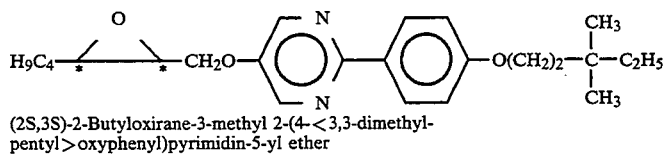

(2S,3S)-2-Butyloxirane-3-methyl 2-(4-<3,3-dimethylpentyl>oxyphenyl)pyrimidin-5-yl ether Phase sequence: X 96 I. $[\alpha]^{22} = -19.6°$ (c=2, $CH_2Cl_2$)

EXAMPLE 29

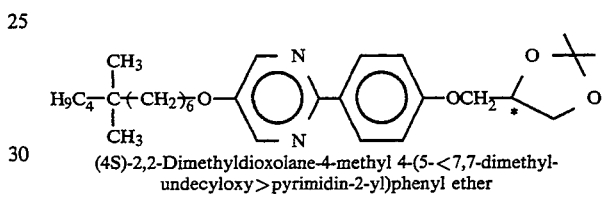

(4S)-2,2-Dimethyldioxolane-4-methyl 4-(5-<7,7-dimethylundecyloxy>pyrimidin-2-yl)phenyl ether Phase sequence: X 110 I. $[\alpha]_D^{22} = +6.06°$ (c=2, $CH_2Cl_2$)

EXAMPLE 30

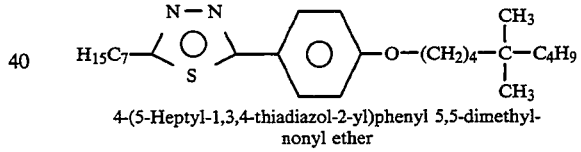

4-(5-Heptyl-1,3,4-thiadiazol-2-yl)phenyl 5,5-dimethylnonyl ether

Phase sequence: X 49 $S_c$ 33 I.

EXAMPLE 31

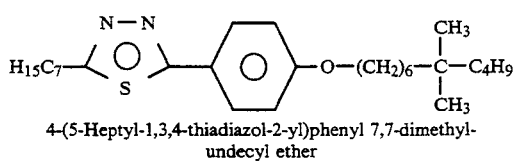

4-(5-Heptyl-1,3,4-thiadiazol-2-yl)phenyl 7,7-dimethyl-
undecyl ether

Phase sequence: X 54 $S_c$ 55 I.

EXAMPLE 32

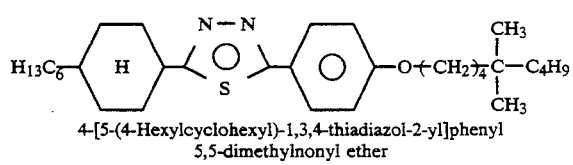

4-[5-(4-Hexylcyclohexyl)-1,3,4-thiadiazol-2-yl]phenyl
5,5-dimethylnonyl ether

Phase sequence: X 93 $S_c$ 101 $S_A$ 111 N 112 I.

EXAMPLE 33

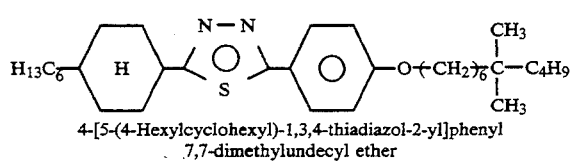

4-[5-(4-Hexylcyclohexyl)-1,3,4-thiadiazol-2-yl]phenyl
7,7-dimethylundecyl ether

Phase sequence: X 90 $S_c$ 117 $S_A$ 192 N 129 I.

Comparative Example C33

A comparison is offered by the following non-dimethyl-substituted compound:

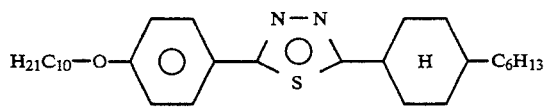

phase sequence: X 105 $S_c$ 122 N165 I.

This example shows that the compounds 33 and 32 according to the invention have a melting point which is 15° C. lower.

EXAMPLE 34

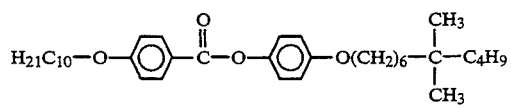

4-(4-Decyloxybenzoyloxy)phenyl 7,7-dimethylundecyl ether

Phase sequence: X 23 $S_B$ 30 $S_c$ 54 $S_A$ 62 I.

EXAMPLE 35

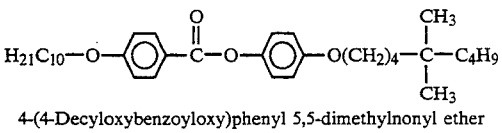

4-(4-Decyloxybenzoyloxy)phenyl 5,5-dimethylnonyl ether

Phase sequence: $X_1$ 29 $X_2$ 38 $S_c$ 39 $S_A$ 48 I.

Comparative Example C35

A comparison is offered by the following non-dimethyl-substituted compound:

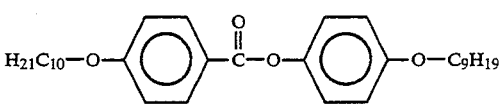

Phase sequence (see Flüssige Kristalle in Tabellen I [Liquid Crystals in Tables I], Deutscher Verlag für Grundstoffindustrie VEB (Leipzig), 1974, page 69, No. 672).

X 75 $S_c$ 87 $S_A$ 89 N 91.

The branched compound has the advantage of a melting point which is 27° C. lower.

EXAMPLE 36

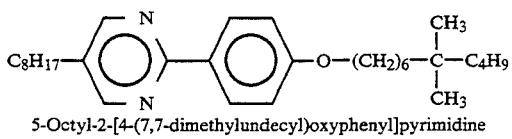

5-Octyl-2-[4-(7,7-dimethylundecyl)oxyphenyl]pyrimidine

Phase sequence: X 9 $S_c$ 29 $S_A$ 46 I.

Comparative Example C36

A comparison is offered by the following non-dimethyl-substituted compound:

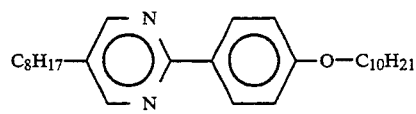

Phase sequence: X 33.5 $S_c$ 61 $S_A$ 67 N 70 I.

The compound according to the invention has the advantage that its melting point is 24° C. lower.

EXAMPLE 37

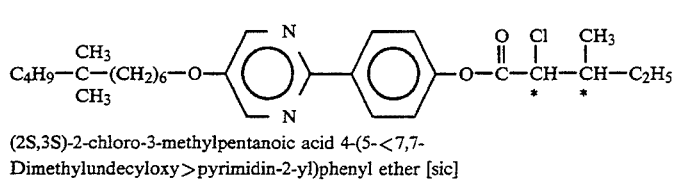

(2S,3S)-2-chloro-3-methylpentanoic acid 4-(5-<7,7-Dimethylundecyloxy>pyrimidin-2-yl)phenyl ether [sic]

Phase sequence: X 22 I.
$[\alpha]_D^{22} = +7.3°$ (c=2, $CH_2Cl_2$)

Use Example 1 a) In order to investigate the effect of the geminally dimethyl-substituted compounds on the effective tilt angle, 10% of various compounds were in each case dissolved in the following ferroelectric mixture M comprising 10 components:

with the analogous unsubstituted or monomethyl-substituted alkyl compounds.

TABLE I

Correlation between structure and contrast

| Example No. | Structure of the 10% mixture constituent in mixture M | Effective tilt angle |
|---|---|---|
|  | pure base mixture M | 6.5 |
|  | $C_8H_{17}-O-[pyrimidine]-[phenyl]-O-C_8H_{17}$ | 7.2 |
|  | $C_9H_{19}-O-[pyrimidine]-[phenyl]-O-(CH_2)_5-CH(CH_3)(C_2H_5)$ | 7.7 |
|  | $C_9H_{19}-O-[pyrimidine]-[phenyl]-O-(CH_2)_5-C(CH_3)_2-CH_3$ | 8.1 |
|  | $C_8H_{17}-S-[pyrimidine]-[phenyl]-O-C_9H_{19}$ | 7.1 |
|  | $C_7H_{15}-S-[pyrimidine]-[phenyl]-O-C_8H_{17}$ | 6.7 |
|  | $C_9H_{19}-S-[pyrimidine]-[phenyl]-O-(CH_2)_5-CH(CH_3)(C_2H_5)$ | 6.9 |
|  | $C_7H_{15}-S-[pyrimidine]-[phenyl]-O-(CH_2)_5-CH(CH_3)(C_2H_5)$ | 7.5 |
|  | $C_{10}H_{21}-S-[pyrimidine]-[phenyl]-O-(CH_2)_5-C(CH_3)_2-CH_3$ | 8.7 |

Mixture M:

| 5-Octyloxy-2-(4-hexyloxyphenyl)pyrimidine | 10.5 mol % |
|---|---|
| 5-Octyloxy-2-(4-octyloxyphenyl)pyrimidine | 4.8 mol % |
| 5-Octyloxy-2-(4-butyloxyphenyl)pyrimidine | 11.1 mol % |
| 5-Octyloxy-2-(4-decyloxyphenyl)pyrimidine | 8.8 mol % |
| 4-(5-Dodecylpyrimidin-2-yl)[phenyl] [sic] trans-4-pentylcyclohexanecarboxylate | 16.6 mol % |
| 5-Octyl-2-(4-decyloxyphenyl)pyrimidine | 11.2 mol % |
| 5-Octyl-2-(4-octyloxyphenyl)pyrimidine | 15.2 mol % |
| 5-Octyl-2-(4-hexyloxyphenyl)pyrimidine | 16.8 mol % |
| 4-(2-Octyloxypyrimidin-5-yl)phenyl (2R,3R)-3-propyloxirane-2-carboxylate | 0.9 mol % |
| (R)-4-(5-n-Octylpyrimidin-2-yl)phenyl 2,2-dimethyl-1,3-dioxolane-4-carboxylate | 4.1 mol% |

The structure of the compounds and the change in contrast are given in the table below.

The measurement results given in Table 1 show that the use of geminally dimethyl-substituted compounds results in an increase in the effective tilt angle compared Use Example 2 a) A liquid-crystalline mixture comprising the following nine components

| 5-Octyloxy-2-(4-hexyloxyphenyl)pyrimidine | 8.8 mol % |
|---|---|
| 5-Octyloxy-2-(4-octyloxyphenyl)pyrimidine | 3.0 mol % |
| 5-Octyloxy-2-(4-butyloxyphenyl)pyrimidine | 9.6 mol % |
| 5-Octyloxy-2-(4-decyloxyphenyl)pyrimidine | 5.3 mol % |
| 5-Octyl-2-(4-dodecyloxyphenyl)pyrimidine | 7.8 mol % |
| 4-(5-Decylpyrimidin-2-yl)phenyl trans-4-pentylcyclohexanecarboxylate | 12.4 mol % |
| 4-(5-Octylpyrimidin-2-yl)[phenyl] [sic] heptanoate | 13.1 mol % |
| 4''-(5,5-Dimethylnonyloxy)phenyl 4'-decyloxybenzoate | 40.0 mol % | has the following phase ranges:

X —32 $S_c$ 52 $S_A$ 65 N 75 I.

The crystallization point at a cooling rate of 10° C. min$^{-1}$ is −40° C.

b) In order to compare the physical properties, the phase ranges were measured of a mixture which differs from the abovementioned mixture only in that it contains no component according to the invention. This comparative mixture has the following phase ranges:

X −9 S$_c$ 73 S$_A$ 77 N 96 I.

The crystallization point under the abovementioned cooling conditions is −17° C. The component according to the invention obviously results in a reduction in the melting point and crystallization point.

Use Example 3

A ferroelectric liquid-crystalline mixture comprising six components

| | |
|---|---|
| 5-Octyloxy-2-(4-butyloxyphenyl)pyrimidine | 25.2 mol % |
| 5-Octyloxy-2-(4-hexyloxyphenyl)pyrimidine | 24.0 mol % |
| 5-Octyloxy-2-(4-octyloxyphenyl)pyrimidine | 11.4 mol % |
| 5-Octyloxy-2-(4-decyloxyphenyl)pyrimidine | 20.2 mol % |
| 4-(5-Decylpyrimidin-2-yl)phenyl trans-4-pentylcyclohexanecarboxylate | 14.2 mol % |
| (2S,3S)-2-[4-(5-(5,5-Dimethylnonyl)pyrimidin-2-yl)phenyloxy]methyl-3-butyloxirane | 5.0 mol % | has the following liquid-crystalline phase ranges:

X 11 S$_c$* 79 S$_A$* 84 N* 97 I and has, at 2° C. [sic], a spontaneous polarization of 37 nC·cm$^{-2}$ and a switching time of 80 μs.

By comparison, the ferroelectric mixture which differs from the abovementioned ferroelectric mixture only in that the dope according to the invention is replaced by 5 mol-% of (octyloxypyrimidin-2-yl)phenyl (2R,3R)-3-propyloxirane-2-carboxylate has, at a temperature of 20° C., a polarization of 24 nC·cm$^{-2}$ and a switching time of 120 μs.

The dimethyl-substituted dope is obviously distinguished by the fact that it induces in mixtures a spontaneous polarization which is 1.5 times higher than in the comparable dope mixture.

A further advantage is that the ferroelectric liquid-crystalline mixture containing the dope according to the invention has a significantly shorter switching time than the comparative mixture.

We claim:

1. A geminal dimethylalkyl compound of the formula (I)

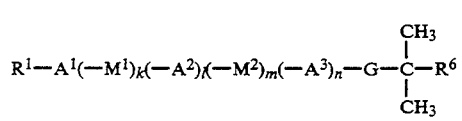

in which:

R$^1$ is CH$_3$, straight-chain or branched (with or without an asymmetric carbon atom) alkyl having 2 to 16 carbon atoms, it also being possible for one or two non-adjacent —CH$_2$— groups to be replaced by —O—, —CO—O—, —O—CO—, or is one of the following radicals

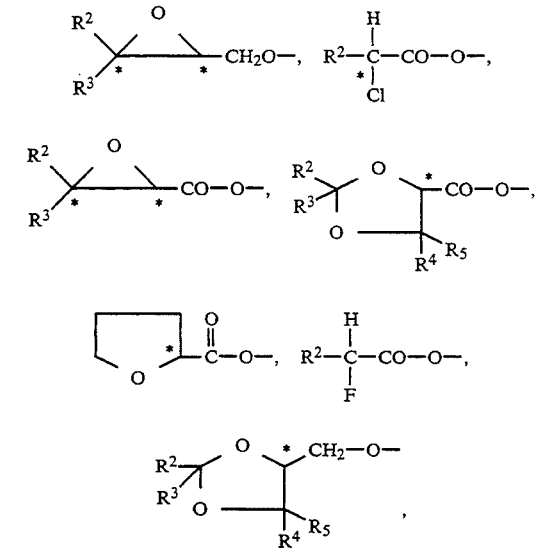

A$^1$, A$^2$ and A$^3$ are identical or different 1,4-phenylene, in which 2H may be replaced by F, 1,4-cyclohexylene, pyridine-2,5-diyl, pyrimidine-2,5-diyl or (1,3,4)-thiadiazole-2,5-diyl, M$^1$ and M$^2$ are identical or different —CO—O—, —O—CO—, G and is straight-chain or branched alkylene having 1 to 16 carbon atoms in which, in addition, one —CH$_2$— group may be replaced by —O—, —O—CO—, —CO—O—, R$^2$, R$^3$, R$^4$ and R$^5$ are identical or different, H or straight-chain or branched alkyl having 1 to 16 carbon atoms, k, l, m and n are zero or 1, and R$^6$ is straight-chain alkyl having 1 to 10 carbon atoms.

2. A geminal dimethylalkyl compound as claimed in claim 1, wherein, in the formula I, the —A$^1$(—M$^1$)$_k$(—A$^2$)$_l$(—M$^2$)$_m$(—A$^3$)$_n$— group is:

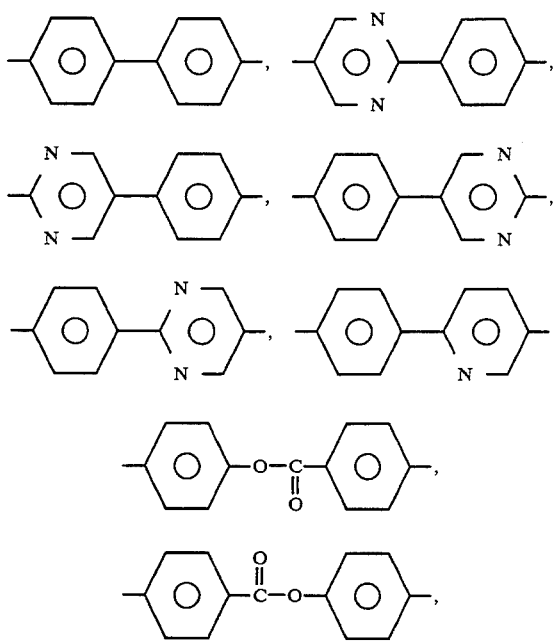

-continued

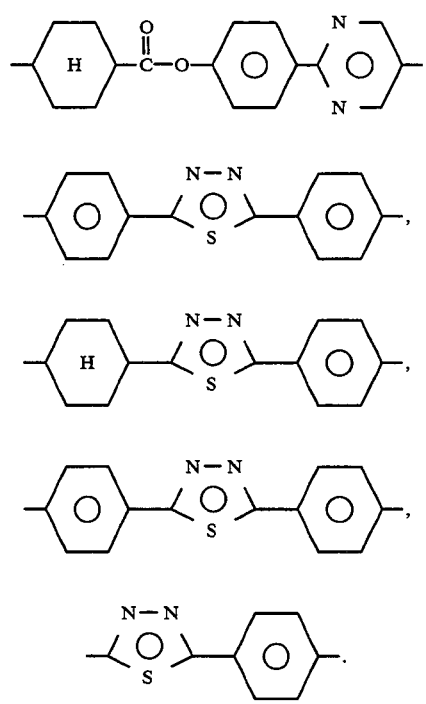

3. A geminal dimethylalkyl compound as claimed in claim 1, wherein, in the formula I, the —A$^1$(—M$^1$)$_k$(—A$^2$)$_l$(—M$^2$)$_m$(—A$^3$)$_n$— group has the following meanings:

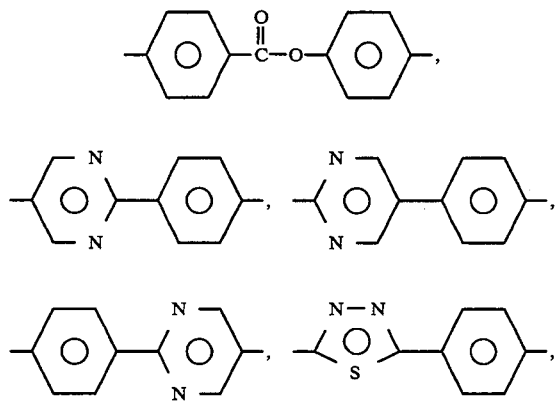

-continued

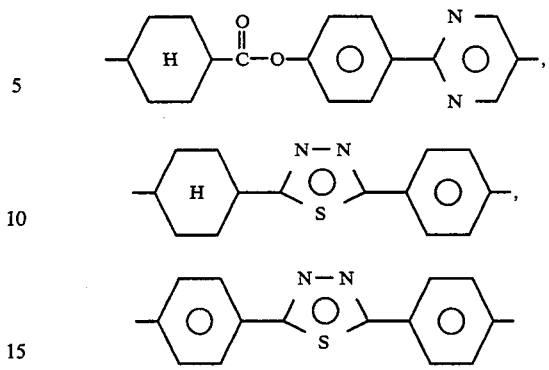

R$^1$ is: straight-chain or branched (with or without an asymmetric carbon atom) alkyl having 2 to 16 carbon atoms, it also being possible for one CH$_2$ group to be replaced by —O—, —CO—O— or —O—CO—, G is: straight-chain or branched alkylene having 1 to 16 carbon atoms in which, in addition, one —CH$_2$— group may be replaced by —O—, —CO—O— or —O—CO—, and R$^6$ is: straight-chain alkyl having 1 to 6 carbon atoms.

4. A liquid-crystalline mixture containing at least one geminal dimethylalkyl compound of the formula (I) as claimed in claim 1.

5. An electrooptical switching and display device containing a liquid-crystalline mixture as claimed in claim 4.

6. A liquid-crystalline mixture containing at least one geminal dimethylalkyl compound of the formula (I) as claimed in claim 2.

7. A liquid-crystalline mixture containing at least one geminal dimethylalkyl compound of the formula (I) as claimed in claim 3.

8. A liquid-crystalline mixture as claimed in claim 4 which is ferroelectric.

9. A liquid-crystalline mixture as claimed in claim 4 which is nematic.

10. A liquid-crystalline mixture as claimed in claim 4, which has 2 to 20 components comprising 0.01 to 70% by weight of at least one geminal dimethylalkyl compound of the formula (I).

11. A method for depressing the melting point of a liquid crystalline mixture which comprises adding 0.01 to 70% by weight of at least one geminal dimethylalkyl compound of the formula (I) as claimed in claim 1 to a liquid-crystalline mixture comprising 2 to 20 components.

* * * * *